United States Patent
Parker et al.

[19]

[11] Patent Number: 5,975,711
[45] Date of Patent: Nov. 2, 1999

[54] INTEGRATED DISPLAY PANEL ASSEMBLIES

[75] Inventors: Jeffery R. Parker, Strongsville; Mark D. Miller, Parma; Daniel N. Kelsch, Lakewood, all of Ohio

[73] Assignee: Lumitex, Inc., Strongsville, Ohio

[21] Appl. No.: 08/871,391

[22] Filed: Jun. 9, 1997

Related U.S. Application Data

[60] Continuation-in-part of application No. 08/778,089, Jan. 2, 1997, which is a division of application No. 08/495,176, Jun. 27, 1995, Pat. No. 5,613,751.

[51] Int. Cl.[6] .................................................. H04M 1/22
[52] U.S. Cl. ............................... 362/24; 362/27; 362/30; 362/31; 362/88; 200/314
[58] Field of Search .................................. 362/24, 26, 27, 362/30, 31, 85, 86, 88; 200/312, 313, 314, 317; 349/62, 65

[56] References Cited

U.S. PATENT DOCUMENTS

| | | | |
|---|---|---|---|
| 3,328,570 | 6/1967 | Balchunas | 362/31 |
| 3,774,021 | 11/1973 | Johnson | 362/27 |
| 3,892,959 | 7/1975 | Pulles | 362/31 |
| 4,247,747 | 1/1981 | Swatten | 200/314 |
| 4,257,084 | 3/1981 | Reynolds | 362/31 |
| 4,282,560 | 8/1981 | Kringel et al. | 362/26 |
| 4,343,975 | 8/1982 | Sado | 200/314 |
| 4,446,508 | 5/1984 | Kinzie | 362/31 |
| 4,573,766 | 3/1986 | Bournay, Jr. et al. | 349/65 |
| 4,630,895 | 12/1986 | Abdala, Jr. et al. | 362/31 |
| 4,638,131 | 1/1987 | Kidd et al. | 200/61.55 |
| 4,714,983 | 12/1987 | Lang | 362/27 |
| 4,751,615 | 6/1988 | Abrams | 362/31 |
| 4,772,769 | 9/1988 | Shumate | 200/314 |
| 4,789,224 | 12/1988 | Bougsty | 362/31 |
| 4,974,122 | 11/1990 | Shaw | 362/31 |
| 4,975,808 | 12/1990 | Bond et al. | 362/31 |
| 4,978,952 | 12/1990 | Irwin | 345/102 |
| 5,005,108 | 4/1991 | Pristash et al. | 362/31 |
| 5,027,258 | 6/1991 | Schoniger et al. | 362/31 |
| 5,070,431 | 12/1991 | Kitazaun et al. | 362/31 |
| 5,093,765 | 3/1992 | Kashima et al. | 362/31 |
| 5,128,842 | 7/1992 | Kenmochi | 362/31 |
| 5,134,549 | 7/1992 | Yokoyama | 362/31 |
| 5,136,483 | 8/1992 | Schoniger et al. | 362/545 |
| 5,207,493 | 5/1993 | Murase et al. | 362/31 |
| 5,225,818 | 7/1993 | Lee et al. | 200/314 |
| 5,283,673 | 2/1994 | Murace et al. | 349/65 |
| 5,339,179 | 8/1994 | Rudisill et al. | 349/65 |
| 5,349,503 | 9/1994 | Blonder et al. | 362/31 |
| 5,375,043 | 12/1994 | Tokunaga | 362/31 |
| 5,390,085 | 2/1995 | Mari-Roca et al. | 362/31 |
| 5,394,308 | 2/1995 | Watanabe et al. | 362/31 |
| 5,521,342 | 5/1996 | Bartley et al. | 200/314 |
| 5,537,300 | 7/1996 | Kraines et al. | 362/86 |

FOREIGN PATENT DOCUMENTS

| | | |
|---|---|---|
| 2 285 518 | 7/1995 | United Kingdom . |
| 2285518 | 12/1995 | United Kingdom . |
| 9617207 | 6/1996 | WIPO . |

*Primary Examiner*—Alan Cariaso
*Attorney, Agent, or Firm*—Renner, Otto, Boisselle & Sklar, P.L.L.

[57] ABSTRACT

Integrated display panel assemblies include a light conducting panel having opposite sides and an end portion for receiving light from one or more light sources for conduction through the panel. On one of the sides of the panel is a first light emitting area for causing a portion of the conducted light to be emitted from the panel for backlighting an LCD or other display supported by the panel in overlying relation to the first light emitting area. The remainder of the conducted light passes beneath the first light emitting area to other light emitting areas on the panel for illuminating other displays associated with the other light emitting areas.

34 Claims, 2 Drawing Sheets

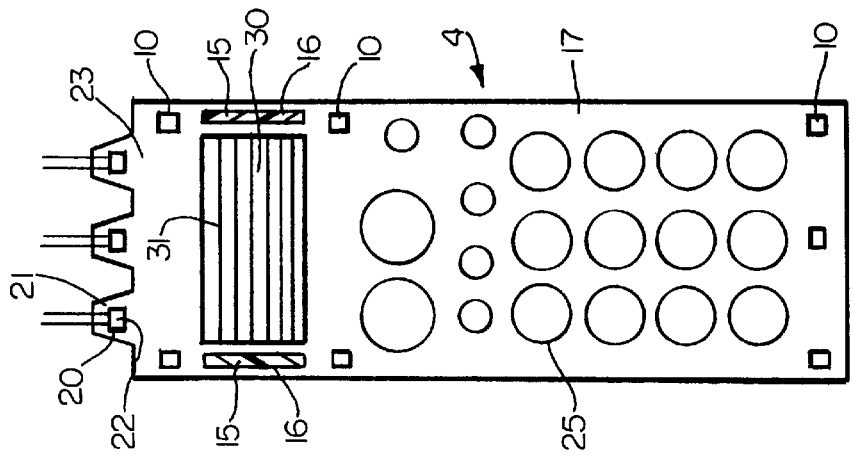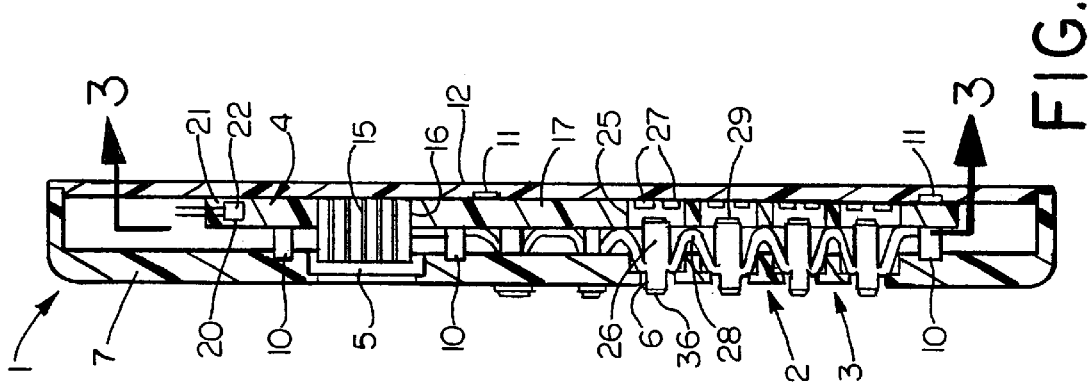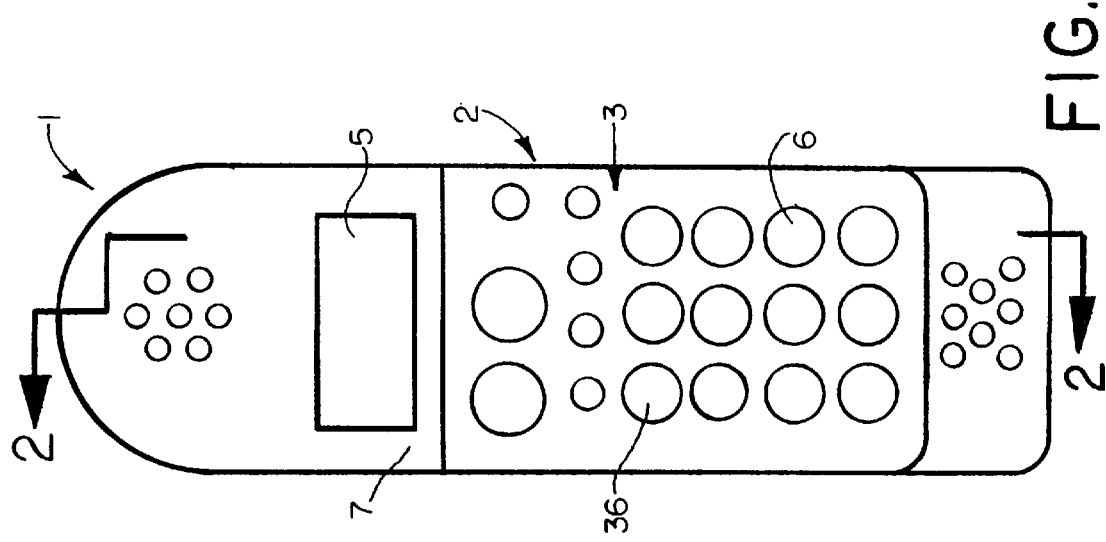

INTEGRATED DISPLAY PANEL ASSEMBLIES

CROSS-REFERENCE TO RELATED APPLICATIONS

This application is a continuation-in-part of U.S. patent application Ser. No. 08/778,089, filed Jan. 2, 1997, which is a division of U.S. patent application Ser. No. 08/495,176, filed Jun. 27, 1995, now U.S. Pat. No. 5,613,751.

FIELD OF THE INVENTION

This invention relates generally to integrated display panel assemblies of the type that include backlight assemblies for backlighting two or more displays associated therewith.

BACKGROUND OF THE INVENTION

It is generally known to provide backlighting for integrated display panel assemblies and the like. This invention relates to certain improvements in the backlight assemblies for such displays which provide more efficient distribution of light to illuminate the displays associated therewith and provide support for the associated displays. As used herein, the term displays means any type of image, key pad, switch and/or legend on a display panel assembly.

SUMMARY OF THE INVENTION

In accordance with one aspect of the invention, the integrated display panel assemblies include backlight assemblies for providing efficient distribution of backlight illumination to two or more displays such as a liquid crystal diode (LCD) and a keyboard of a hand held instrument such as a cellular phone or other such device.

In accordance with another aspect of the invention, the displays are supported by the backlight assembly.

In accordance with another aspect of the invention, the backlight assembly includes a first light emitting area located directly behind an LCD for causing a portion of the light traveling through the backlight assembly to be emitted for backlighting the LCD and causing additional light to pass beneath the first light emitting area to other light emitting areas of the backlight assembly for illuminating one or more other displays on the display panel assembly.

In accordance with another aspect of the invention, a plurality of light emitting diodes (LEDs) are mounted at or near one end of the backlight assembly to provide the light source for illuminating the associated displays.

In accordance with another aspect of the invention, the backlight assembly includes slots for holding and aligning conductors such as zebra strips that extend through the slots and electrically connect an LCD or other display to a printed circuit board (PCB) mounted on the back side of the backlight assembly.

In accordance with another aspect of the invention, a conductive trace may be provided on the front side of the backlight assembly for establishing electrical contact with an LCD or other type of display such as a key pad for performing a switching function.

In accordance with another aspect of the invention, the backlight assembly forms the bottom layer of an LCD.

To the accomplishment of the foregoing and related ends, the invention, then, comprises the features hereinafter fully described and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIG. 1 is a schematic top plan view of one form of integrated display panel assembly in accordance with the invention;

FIG. 2 is a longitudinal section through the assembly of FIG. 1 taken generally along the plane of the line 2—2 thereof;

FIG. 3 is a top plan view of the backlight assembly for the integrated display panel assembly of FIGS. 1 and 2 as generally seen from the plane of the line 3—3 of FIG. 2;

DETAILED DESCRIPTION OF THE PREFERRED EMBODIMENTS

Figure 4:
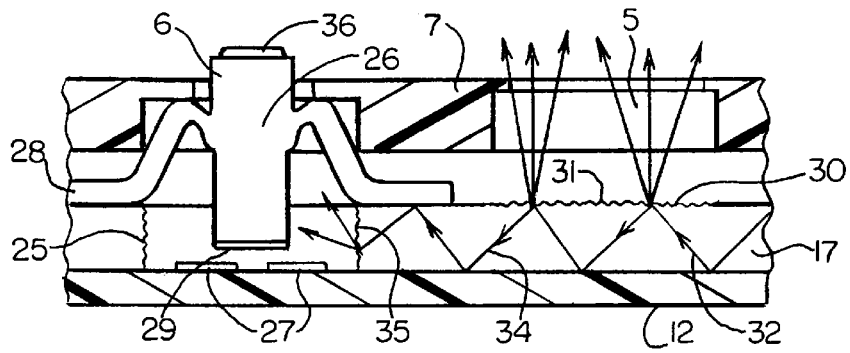
FIG. 4 is an enlarged schematic fragmentary section of a portion of the panel assembly of FIG. 2 in which an LCD and key pad are shown being backlighted by the backlight assembly.

Referring now in detail to the drawings and initially to FIGS. 1 and 2, there is schematically shown one form of integrated display panel assembly or module 1 in accordance with the present invention including a low profile keyboard 2 such as used in a cellular phone or other hand held instrument 3 and a backlight assembly 4 which provides backlight illumination for two or more displays such as a liquid crystal display (LCD) 5 and key pads 6 on the keyboard 2 as described hereafter. The display module 1 includes a bezel 7 which serves as a frame for the LCD 5 and key pads 6. Posts or protuberances 10 on the front side of the backlight assembly 4 provide for alignment and attachment of the bezel, LCD and keyboard layers to the backlight assembly. Similar posts or protuberances 11 on the back side of the backlight assembly provide for alignment and attachment of a printed circuit board (PCB) 12 to such back side using suitable fasteners (not shown).

Conductive traces on the PCB 12 may be electrically connected to the LCD 5 via elastomeric anisotropic conductive sheets 15, commonly referred to as zebra strips. Slots 16 are provided in the backlight assembly 4 (see FIGS. 2 and 3) through which the zebra strips 15 extend for holding and aligning the zebra strips with respect to the LCD 5 and PCB 12. The alignment of these elements is critical in providing the required electrical connections between the LCD and PCB which are mechanically mounted on opposite sides of backlight assembly 4.

Backlight assembly 4 comprises a relatively thin, long panel 17 made of a transparent light conductive material of any suitable type including plastic such as acrylic or polycarbonate, or glass. The light conductive panel 17 may be substantially flat, or curved, may be a single layer or multi-layers, and may have different thicknesses and shapes. Moreover, the panel 17 may be flexible, or rigid, and may be made out of a variety of compounds. Further, the panel 17 may be hollow, filled with liquid, air, or be solid, and there may be holes or ridges in the panel. Panel 17 acts as a light guide for conducting light entering the panel at one or both ends via internal reflections within the panel. A portion of the light is extracted from the panel 17 for backlighting the LCD 5 when needed while the remaining portion of the light passes beneath the LCD for lighting the key pads 6 or other displays.

The surface luminance and uniformity of the escaping light is a function of the type, location and size of deformities or disruptions in the panel 17. A pattern of such light extracting deformities or disruptions may be provided on selected areas on one or both sides of the panel as desired. As used herein, the terms deformities or disruptions are used interchangeably to mean any change in the shape or geometry of the panel surface and/or coating or surface treatment that causes a portion of the light to be emitted. A pattern of light extracting deformities may include a variable pattern which breaks up the light rays such that the internal angle of reflection of a portion of the light rays will be great enough to cause a portion of the light rays either to be emitted out of the panel through the side on which the light extracting deformities are provided or reflected back through the panel and emitted out the other side.

These deformities or disruptions can be produced in a variety of manners, for example, by providing a painted pattern, an etched pattern, machined pattern, a printed pattern, a hot stamped pattern, or a molded pattern or the like on selected light output areas of the panel. An ink or printed pattern may be applied for example by pad printing, silk screening, ink jet, heat transfer film process or the like. The deformities may also be printed on a sheet or film which is used to apply the deformities to the panel. This sheet or film may become a permanent part of the panel for example by attaching or otherwise positioning the sheet or film against one or both sides of the panel in order to produce a desired effect.

By varying the density, opaqueness or translucence, shape, depth, color, area, index of refraction or type of deformities on an area or areas of the panel, the light output from the panel can be controlled. The deformities or disruptions may be used to control the percent of light emitting from any area of the panel. For example, less and/or smaller size deformities may be placed on panel areas where less light output is wanted. Conversely, a greater percentage of and/or larger deformities may be placed on areas of the panel where greater light output is desired.

Varying the percentages and/or size of deformities in different areas of the panel is necessary in order to provide a uniform light output distribution at the different areas. For example, the amount of light traveling through the panel will ordinarily be greater in areas closer to the light source than in other areas further removed from the light source. A pattern of light extracting deformities may be used to adjust for the light variances within the panel, for example, by providing a denser concentration of light extracting deformities with increased distance from the light source thereby resulting in a more uniform light output distribution from the panel.

The deformities may also be used to control the output ray angle distribution of the emitted light to suit a particular application. For example, where the panel is used to provide an LCD backlight, the light output will be more efficient if the deformities cause the light rays to emit from the panel at predetermined ray angles such that they will pass through the LCD with low loss.

Additionally, the pattern of light extracting deformities may be used to adjust for light output variances attributed to light extractions of the panel. The pattern of light extracting deformities may be printed on the light output areas utilizing a wide spectrum of paints, inks, coatings, epoxies, or the like, ranging from glossy to opaque or both, and may employ half-tone separation techniques to vary the deformity coverage. Moreover, the pattern of light extracting deformities may be multiple layers or vary in index of refraction.

Print patterns of light extracting deformities may vary in shape such as dots, squares, diamonds, ellipses, stars, random shapes, and the like. Additionally, the deformities may vary in shape and/or size along the length and/or width of the light output areas of the panel. Also, a random placement pattern of deformities may be utilized throughout the length and/or width of the light output areas of the panel. The deformities may have shapes or a pattern with no specific angle to reduce moire or other interference effects. Examples of methods to create these random patterns are printing a pattern of shapes using strochastic print pattern techniques, frequency modulated half tone patterns, or random dot half tones. Moreover, the deformities may be colored in order to effect color correction in the panel. The colors of the deformities may also vary throughout the panel, for example, to provide different colors for the same or different light output areas.

In addition to or in lieu of the patterns of light extracting deformities previously described, other light extracting deformities including prismatic surfaces, depressions or raised surfaces of various shapes using more complex shapes in a mold pattern may be molded, etched, stamped, thermoformed, hot stamped or the like into or on one or more light output areas of the panel. Prismatic surfaces, depressions or raised surfaces will cause a portion of the light rays contacted thereby to be emitted from the panel. Also, the angles of the prisms, depressions or other surfaces may be varied to direct the light in different directions to produce a desired light output distribution or effect. Moreover, the reflective or refractive surfaces may have shapes or a pattern with no specific angles to reduce moire or other interference effects.

The light conductive panel 17 may have one or more light emitting diodes (LED's) or other light sources placed adjacent one or more ends or sides of the panel, or such light sources may be surface mounted on the panel or otherwise mounted interiorly of the panel. In the embodiment shown in FIGS. 2 and 3, the light conductive panel 17 has a plurality of slots, cavities or openings 20 machined, molded or otherwise formed in one or more optical focus sections 21 at one end of the panel in which one or more LEDs or other light sources 22 are mounted. Preferably the light sources 22 are embedded, potted or bonded in the optical focus sections 21 in order to eliminate any air gaps or air interface surfaces between the light sources and adjacent light transition areas 23 in order to reduce light loss received by the light transition areas and increase the light output emitted by the panel.

Such mounting of the light sources may be accomplished, for example, by bonding the light sources in the slots, cavities or openings 20 using a sufficient quantity of a suitable optically transparent embedding, potting or bonding material. The slots, cavities or openings 20 may be on the top, bottom, sides or ends of the light conductor 17. Bonding can also be accomplished by a variety of methods that do not incorporate extra material, for example, thermal bonding, heat staking, ultrasonic or plastic welding or the like. Other methods of bonding include insert molding and casting around the light sources.

Also, the light sources 22 may be multiple colored LEDs, or a combination of multiple colored radiation sources in order to provide a desired colored or white light output distribution. For example, a plurality of colored lights such as LEDs of different colors (e.g., red, blue and/or green) or a single LED with multiple colored chips may be employed to create white light or any other colored light output distribution by varying the intensities of each individual colored light.

The light conductive panel 17 shown in FIGS. 1 through 3 is made of a relatively rigid transparent material, and has holes 25 therethrough to facilitate motion of switch plunger portions 26 of the key pads 6 into and out of contact with conductors 27 on the PCB 12 which is mounted on the back side of the light conductive panel 17 as schematically shown in FIGS. 2 and 4. The key pads 6 are an integral part of a flexible key pad membrane or panel 28 of accordion design which gives the switch plungers 26 some tactile feedback and returns the key pads to their original raised positions shown in FIGS. 2 and 4 after being depressed to cause the conductors 29 on the switch plungers 26 to short out the associated conductors 27 on the PCB. While the key pads are shown in FIGS. 1 through 3 as being push type switches, it will be apparent that the key pads could be other types of switches. Also, the key pads could be knobs, pointers, indicators, slides, etc. for performing other functions as desired.

The light conductive panel 17 has a light output area 30 immediately behind the LCD 5 containing light extracting deformities or disruptions 31 for causing a portion of the light rays 32 from the light sources 22 to be emitted for backlighting the LCD 5 as schematically shown in FIG. 4.

The remaining portion 34 of the light rays passes through the light conductor 17 beneath the LCD 5 and is scattered into the holes 25 for illuminating the key pads 6 and associated legends 36. If desired, the shape of the holes 25 can be altered, or deformities 35 can be provided around the holes to extract light in a predetermined pattern.

The relatively rigid optically clear light conductor 17 shown in FIGS. 2 through 4 performs other functions in addition to conducting light and illuminating the LCD 5 and key pads 6 and associated legends 36. In particular, the light conductor 17 serves as a spacer separating the flexible key pad membrane or panel 28 and bezel 7 from the PCB 12 and acts as a structural member and guide for the switch plungers 26.

Figure 5:
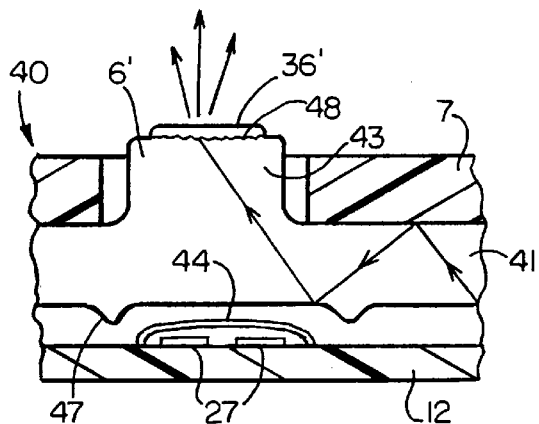
FIGS. 5 and 6 are enlarged schematic fragmentary sections of portions of other panel assembly embodiments in accordance with this invention in which key pads or other displays are integrally formed on the backlight assemblies.

FIG. 5 shows a modified form of display module 40 in accordance with this invention in which the light conductive panel 41 comprises a continuous, flexible optically clear panel with protrusions 43 thereon which form the key pads 6', thus eliminating the need for a separate key pad membrane. In this embodiment, the switching function is accomplished by depressing the key pads 6' and thus the panel 41 into pressure engagement with domes 44 therebeneath. The domes 44 are bimetallic springs which are stable in the convex position shown in FIG. 5. However, when pressure is applied to the domes 44 through the key pads 6', the domes snap to a flat position, giving a tactile feedback and shorting out associated conductors 27 on the PCB to complete the switching function. Also, the light conductive panel 41 may include annular protrusions 47 on the bottom surface thereof surrounding the domes 44 for keeping or retaining the domes in overlying relation to the associated conductors 27 on the PCB. Light conducted to the key pads 6' exits at the key pad legends 36' by any number of ways, such as scattering from deformities 48 on the key pads or refraction.

Figure 6:
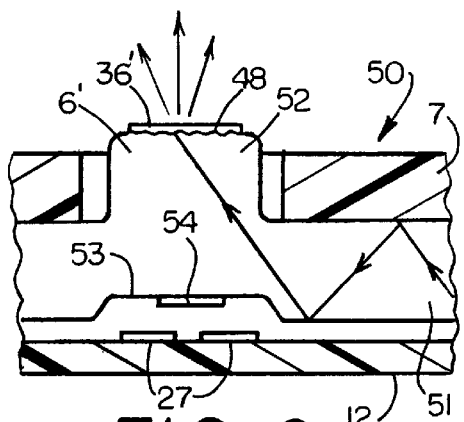

FIG. 6 shows another form of display module 50 in accordance with this invention which also includes a flexible, optically clear light conductive panel 51 having protrusions 52 thereon forming the key pads 6'. However, in this embodiment recesses 53 are provided in the bottom side of the panel 51 in line with the key pad protrusions 52. Within the recesses 53 are conductors 54. When the key pads 6' are depressed, the conductors 54 make contact with associated switch contacts 27 on the PCB 12, shorting them out to complete the switching function. Here again, light conducted to the key pads 6' exits at the key pad legends 36' by scattering from deformities 48 or refraction in the manner previously described.

Figure 7:
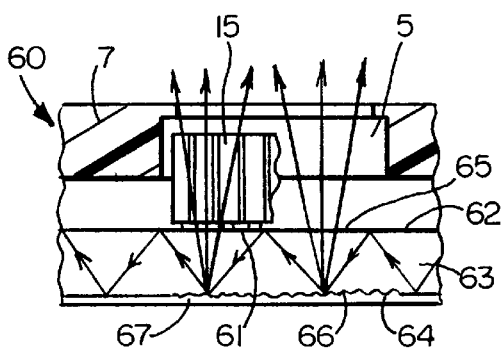
FIGS. 7 through 9 are enlarged schematic fragmentary sections through modified forms of panel assemblies in accordance with this invention.

FIG. 7 shows a modified form of display module 60 in accordance with this invention in which a conductive trace 61 of the PCB is printed on the top surface 62 of a flexible or rigid light conductive panel 63 thus eliminating the need for the PCB. On the bottom surface 66 of the panel 63 directly opposite the conductive trace 61 are deformities 64 for causing a portion of the light to be directed back through the panel and emitted from the light emitting area 65 immediately behind the LCD 5 in a predetermined pattern. The bottom surface 66 of the panel may also be provided with a reflective coating 67 in order to improve light output efficiency of the panel by reflecting any light emitted from the bottom surface back through the panel for emission from the light emitting area 65.

Figure 8:
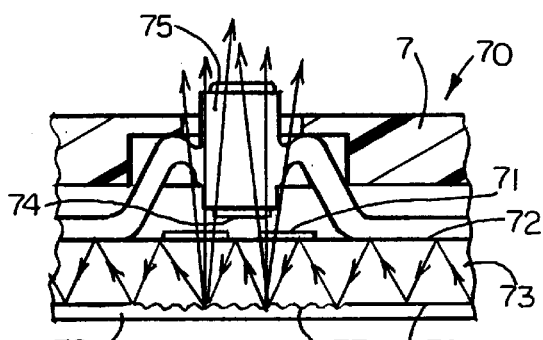

FIG. 8 shows another form of display module 70 in accordance with this invention in which a conductive trace 71 of the PCB is printed on the top surface 72 of a flexible or rigid light conductive panel 73 for selective contact by conductors 74 on the key pads 75, thus eliminating the need for the PCB. On the bottom surface 76 of the panel 73 directly opposite the key pads 75 are deformities 77 for causing a portion of the light to be directed back through the panel for backlighting the key pads. A reflective coating 78 may also be provided on such bottom surface 76 for redirecting any light emitted from the bottom surface back through the panel.

Figure 9:
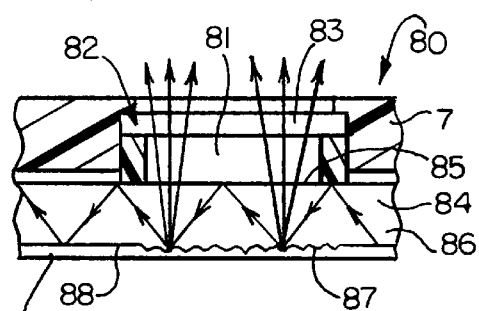

FIG. 9 shows still another form of display module 80 in accordance with this invention in which the liquid crystal material 81 of an LCD 82 is disposed between the top glass layer 83 and a bottom layer 84 formed by a light emitting area 85 of a flexible or rigid light conductive panel 86. Thus, in this particular embodiment, the bottom layer of the LCD provides the desired backlighting for the LCD. Also in this embodiment, the deformities 87 for causing a portion of the light to be emitted for backlighting the LCD 82 are provided on the bottom surface 88 of the panel. A reflective coating 89 on such bottom surface redirects any light emitted from the bottom surface back through the panel. Polarizing films (not shown) may be provided on the top glass layer 83 of the LCD 82 and between the liquid crystal material 81 and the light conductive panel 86.

Although the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims.

What is claimed is:

1. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, and an other display associated with said other light emitting area, said first display comprising a liquid crystal display supported by said panel.

2. The assembly of claim 1 wherein said other display comprises key pads of a keyboard supported by said panel.

3. The assembly of claim 2 wherein said panel includes posts for aligning and attaching said liquid crystal display and said keyboard to said panel.

4. The assembly of claim 2 further comprising a bezel surrounding said liquid crystal display and said key pads, said panel including posts for aligning and attaching said bezel to said panel.

5. The assembly of claim 1 further comprising a printed circuit board attached to an other side of said panel, slots in said panel, and conductors extending through said slots for electrically connecting said liquid crystal display to said printed circuit board.

6. The assembly of claim 5 wherein said conductors comprise zebra strips, said slots holding and aligning said zebra strips with respect to said liquid crystal display and said printed circuit board.

7. The assembly of claim 1 wherein said liquid crystal display includes a top layer, a bottom layer formed by said panel, and liquid crystal material between said layers.

8. The assembly of claim 7 wherein deformities are provided on an other side of said panel opposite said first light emitting area to cause a portion of the conducted light to be emitted from said first light emitting area.

9. The assembly of claim 1 wherein said other display comprises key pads on said one side of said panel, said panel being made of a flexible material, whereby when said key pads are depressed, a portion of said panel moves correspondingly.

10. The assembly of claim 9 wherein said key pads are integrally molded on said panel.

11. The assembly of claim 9 further comprising a printed circuit board adjacent an other side of said panel having circuitry thereon which is actuated by depressing the respective key pads on said panel.

12. The assembly of claim 1 further comprising a conductive trace on said one side of said panel, and conductors for establishing electrical contact between one of said displays and said conductive trace.

13. The assembly of claim 1 further comprising a light source for supplying light to said end portion of said panel.

14. The assembly of claim 13 wherein said light source comprises one or more light emitting diodes embedded or potted in said panel.

15. The assembly of claim 1 further comprising a light source mounted in a recess, slot or cavity in said end portion of said panel.

16. The assembly of claim 1 wherein said panel includes an optical focus section adjacent said end portion of said panel containing a light source, and a light transition area intermediate said optical focus section and said end portion.

17. A display panel assembly comprising light conducting panel having opposite sides and an end portion containing a light source for providing light that is conducted through said panel, a first light emitting area on one of said sides from which a portion of the conducted light is emitted from said panel for backlighting a liquid crystal display overlying said first light emitting area, the remaining portion of the conducted light passing beneath said first light emitting area to other light emitting areas on said panel where additional light is emitted for lighting other displays associated with said other light emitting areas.

18. The assembly of claim 17 wherein said other displays comprise a plurality of key pads.

19. The assembly of claim 18 further comprising a conductive trace on said one side of said panel, and conductors for establishing electrical contact between said liquid crystal display or said key pads and said conductive trace.

20. The assembly of claim 17 further comprising a printed circuit board attached to an other side of said panel, said panel having slots for holding and aligning zebra strips with respect to said liquid crystal display and said printed circuit board, said zebra strips extending through said slots for establishing electrical contact between said liquid crystal display and said printed circuit board.

21. The assembly of claim 17 wherein said light source comprises a plurality of light emitting diodes embedded or potted in said end portion of said panel.

22. The assembly of claim 21 further comprising recesses, slots or cavities in said end portion containing said light emitting diodes, said recesses, slots or cavities being filled with a transparent medium to eliminate any air interface between said light emitting diodes and said panel.

23. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, and an other display associated with said other light emitting area, said assembly comprising a hand held instrument including a liquid crystal display as said first display and key pads as said other display.

24. The assembly of claim 23 wherein said hand held instrument comprises a cellular phone.

25. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, an other display associated with said other light emitting area, and a printed circuit board attached to an other side of said panel, said other display comprising key pads having portions extending through holes in said panel, said key pads when depressed causing contact with said printed circuit board to complete associated circuitry, said holes comprising said other light emitting area for causing light to be emitted around said key pads.

26. The assembly of claim 25 wherein said key pads are carried by a flexible panel which provides tactile feedback to said key pads causing said key pads to return to their original positions when released after being depressed.

27. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, an other display associated with said other light emitting area, a conductive trace on said one side of said panel, and conductors for establishing electrical contact between one of said displays and said conductive trace, said first display comprising a liquid crystal display and said other display comprising key pads, said conductors establishing electrical contact between said liquid crystal display or said key pads and said conductive trace.

28. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, an other display associated with said other light emitting area, and a light source mounted in a recess, slot or cavity in said end portion of said panel, said recess, slot or cavity being filled with a transparent medium to eliminate any air interface between said light source and said panel.

29. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, an other display associated with said other light emitting area, and a light source insert molded or cast within said end portion of said panel.

30. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, an other display associated with said other light emitting area, and a light source bonded to said end portion of said panel so as to eliminate any air interface between said light source and said panel.

31. The assembly of claim 30 further comprising a recess, slot or cavity in said end portion in which said light source is bonded.

32. A display panel assembly comprising a light conducting panel having opposite sides and an end portion for receiving light from one or more light sources for conduction through said panel, a first light emitting area on one of said sides through which a portion of the conducted light is emitted from said panel while the remaining portion of the conducted light passes beneath said first light emitting area to another light emitting area on said panel where additional light is emitted from said panel, a first display overlying said first light emitting area, and an other display associated with said other light emitting area, said panel including an optical focus section adjacent said end portion of said panel containing a light source, and a light transition area intermediate said optical focus section and said end portion, said light source being embedded or potted in said optical focus section to eliminate any air interface between said light source and said light transition area.

33. The assembly of claim 32 wherein said light source comprises a light emitting diode.

34. The assembly of claim 32 wherein said light source comprises a plurality of light emitting diodes.

* * * * *